United States Patent [19]

Nonomura

[11] Patent Number: 5,688,981
[45] Date of Patent: Nov. 18, 1997

[54] ETHYLENEDIAMINETRIACETIC ACID AND N-ACYL ETHYLENEDIAMINETRIACETIC ACID SILVER CHELATING AGENTS AND SURFACTANTS

[75] Inventor: Arthur M. Nonomura, Boxborough, Mass.

[73] Assignee: Hampshire Chemical Corp., Lexington, Mass.

[21] Appl. No.: 749,364

[22] Filed: Nov. 21, 1996

[51] Int. Cl.$^6$ ............................................. C07F 1/10
[52] U.S. Cl. ............................. 556/116; 556/117
[58] Field of Search ........................ 556/116, 117

[56] References Cited

U.S. PATENT DOCUMENTS 4,741,831  5/1988  Ginstead ................... 210/638
5,250,728  10/1993  Parker et al. ............... 562/565
5,284,972  2/1994  Parker et al. ............... 562/565
5,447,602  9/1995  Sajbel et al. ................. 162/6

OTHER PUBLICATIONS

The Merck Index, an enclyclopedia of chemical, drugs, and biologicals, tenth edition 1983; pp. 1221–1224.

Sherwood Medical Thermazene label (4–pages) (1995).

*Primary Examiner*—Porfirio Nazario-Gonzalez
*Attorney, Agent, or Firm*—Nields, Lemack & Dingman

[57] ABSTRACT

Silver chelating agent and surfactant that exhibits photosensitivity and antimicrobial activity. The silver can be chelated with ethylenediaminetriacetic acid (ED3A) or salts thereof, or preferably with N-acyl ED3A or salts thereof. Antimicrobial activity is exhibited even at very low silver levels.

13 Claims, No Drawings

ETHYLENEDIAMINETRIACETIC ACID AND N-ACYL ETHYLENEDIAMINETRIACETIC ACID SILVER CHELATING AGENTS AND SURFACTANTS

BACKGROUND OF THE INVENTION

Ethylenediaminetriacetic acid (ED3A) and its salts (such as ED3ANa$_3$) have applications in the field of chelating chemistry, and may be used as a starting material in the preparation of strong chelating polymers, oil soluble chelants, surfactants and others. Conventional routes for the synthesis of ethylenediaminetriacetic acid were achieved via its N-benzyl derivative, which was subsequently hydrolyzed in alkaline solutions to ED3ANa$_3$, thus avoiding cyclization to its 2-oxo-1,4-piperazinediacetic acid (3KP) derivative.

U.S. Pat. No. 5,250,728, the disclosure of which is hereby incorporated by reference, discloses a simple process for the synthesis of ED3A or its salts in high yield. Specifically, a salt of N,N'-ethylenediaminediacetic acid (ED2AH$_2$) is condensed with stoichiometric amounts, preferably slight molar excesses of, formaldehyde, at temperature between 0° and 110° C., preferably 0° to 65° C. and pH's greater than 7.0 to form a stable 5-membered ring intermediate. The addition of a cyanide source, such as gaseous or liquid hydrogen cyanide, aqueous solutions of hydrogen cyanide or alkali metal cyanide, in stoichiometric amounts or in a slight molar excess, across this cyclic material at temperatures between 0° and 110° C., preferably between 0° and 65° C., forms ethylenediamine N,N'-diacetic acid-N'-cyanomethyl or salts thereof (mononitrile-diacid). The nitrile in aqueous solutions may be spontaneously cyclized in the presence of less than 3.0 moles base: mole ED2AH$_2$, the base including alkali metal or alkaline earth metal hydroxides, to form 2-oxo-1,4-piperazinediacetic acid (3KP) or salts thereof, which is the desired cyclic intermediate. In the presence of excess base, salts of ED3A are formed in excellent yield and purity. This patent also discloses an alternative embodiment in which the starting material is ED2AH$_a$X$_b$, where X is a base cation, e.g., an alkali or alkaline earth metal, a is 1 to 2, and b is 0 to 1 in aqueous solutions. The reaction mixture also can be acidified to ensure complete formation of carboxymethyl-2-oxopiperazine (the lactam) prior to the reaction. Formaldehyde is added, essentially resulting in the hydroxymethyl derivative. Upon the addition of a cyanide source, 1-cyanomethyl-4-carboxymethyl-3-ketopiperazine (mononitrile monoacid) or a salt thereof is formed. In place of CH$_2$O and a cyanide source, HOCH$_2$CN, which is the reaction product of formaldehyde and cyanide, may also be employed in this method. Upon the addition of any suitable base or acid, this material may be hydrolyzed to 3KP. The addition of a base will open this ring structure to form the salt of ED3A.

U.S. Pat. No. 5,284,972, the disclosure of which is hereby incorporated by reference, discloses N-acyl ED3A derivatives and a process for producing the same. The production of N-acyl derivatives of ethylenediaminetriacetic acid can be accomplished according to the following general reaction scheme:

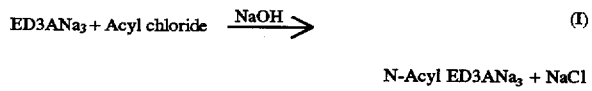

ED3ANa$_3$ + Acyl chloride $\xrightarrow{\text{NaOH}}$ (I)

N-Acyl ED3ANa$_3$ + NaCl

The starting ED3A derivative can be the acid itself, or suitable salts thereof, such as alkali metal and alkaline earth metal salts, preferably sodium or potassium salts.

N-Acyl ED3A salts are mild, biodegradable anionic surfactants. Suitable acyl groups can be of various acyl chain length, and include lauroyl (C$_{12}$), myristoyl (C$_{14}$), cocoyl (C$_{8-18}$) and oleoyl (C$_{18}$).

Silver has long been known to be antimicrobial. For instance, newborns were routinely swabbed with silver nitrate to prevent blinding eye infections until the past decade when nitrates were indicated to cause other problems. Some germicidal silver compounds are limited to topical application and are generally irritating to caustic, often with inconsistent efficacy. Oral administration of silver nitrate can cause severe gastroenteritis which may be fatal. Silver sulfadiazine is commonly used as an antibiotic burn dressing in the form of a topical cream containing 1% silver sulfadiazine in micronized form. It has antimicrobial activity and is bactericidal for gram-negative and gram-positive bacteria. Other germicidal silver compounds include silver lactate, silver picrate, silver oxide, silver iodide and silver citrate, all of which are astringent. These silver compounds have an undesirable propensity towards protein precipitation at $10^{-4}$M concentration, therefore, the chemistry has been fundamentally limited to high dosage.

It would be desirable to provide a silver chelating agent and surfactant that has the potential to provide penetration while carrying silver ion into silver-sensitive pathogens with effective antimicrobial function, including germicidal and antibiotic function, while at low concentrations that are not inhibitory or damaging to host function.

It further would be desirable to develop a novel antibiotic effective against strains of bacteria resistant to conventional antibiotics such as penicillin.

SUMMARY OF THE INVENTION

The problems of the prior art have been overcome by the present invention, which provides novel silver chelating agent and surfactants that exhibit photosensitivity and antimicrobial activity. The silver can be chelated with ethylenediaminetriacetic acid (ED3A) or salts thereof, or preferably with N-acyl ED3A or salts thereof. Antimicrobial activity is exhibited even at very low silver levels.

DETAILED DESCRIPTION OF THE INVENTION

Ethylenediaminetriacetic acid and salts thereof can be prepared as disclosed in U.S. Pat. No. 5,250,728, or by other conventional means. Similarly, N-acyl ethylenediaminetriacetic acid and salts thereof can be prepared as disclosed in U.S. Pat. No. 5,250,728.

Suitable acyl groups for the starting N-acyl derivative of ethylenediaminetriacetic acid ("ED3A") are straight or branched aliphatic or aromatic groups containing from 1 to 40 carbon atoms, preferably acyl groups that are carboxylic acid derivatives. Examples of preferred acyl groups are pentanoyl, hexanoyl, heptanoyl, octanoyl, naananoyl, decanoyl, lauroyl, myristoyl, palmitoyl, oleoyl, stearoyl, nonanoyl, neopentanoyl, neoheptanoyl, neodecanoy, iso-octanoyl, iso-nananoyl, isotridecanoyl, benzoyl and naphthoyl. Lauroyl, myristoyl, cocoyl and oleoyl ethylenediaminetriacetic acid are particular preferred, with the lauroyl derivative being most preferred. The N-acyl ED3A starting material is preferably used in the form of its salt, most preferably its alkali metal salt, particulary sodium or potassium.

Where the ED3A acid or the N-acyl ED3A acid is produced, it can be readily converted into a salt by partial or complete neutralization of the acid with the appropriate base. Similarly, the acid also can be produced from the corresponding ED3A salts or N-acyl ED3A salts by neutralization with a quantitative amount of acid.

In order to produce the silver chelating agent and surfactant of the present invention, silver, such as in the form of silver acetate hydrate or silver carbonate, is dissolved in an aqueous solution of the salt of N-acyl ED3A or ED3A at 50°–80° C. or silver powder is dissolved over time into N-acyl ED3A acid or ED3A acid at approximately 80° C. The amount of silver should be in a ratio to the ED3A or N-acyl ED3A of about 1:3.5; lower ratios (such as 1:2) do not completely dissolve due to lack of sufficient chelation. Sonication is preferably used to enhance the process. The resulting clear solution has an amber hue, becoming a slight purple to gray hue with short exposure to light. Continued exposure to light (especially ultraviolet light) darkens the solution over time to blackness. Accordingly, the solutions preferably should be stored in complete darkness.

The silver chelating agent and surfactant of the present invention exhibits antimicrobial activity against a variety of bacteria, including Escherichia, Klebsiella, Pseudomonas and Staphylococcus. The low toxicity of the chelating agent and surfactant together with the high bioavailability of the chelated silver make the compositions of the invention useful for topical, injected or oral treatment. A topical composition can be in the form of a cream, such as a mixture with an aquaphor cream base. A water-based liquid also could be used, with application by swabbing or spraying. Penetration aided by surfactant action allows for very low effective doses, such as 10 parts per million (ppm).

Against some bacteria, such as *Escherichia coli* and *Klebsiella terrigena*, the Minimum Lethal Concentration (MLC) and the Minimum Inhibitory Concentration (MIC) of the silver chelating agent and surfactant of the present invention are 10 ppm silver. At such a low silver concentration, it is unlikely that a suitable dosage will be toxic to the host. Accordingly, the silver chelating agent and surfactant of the present invention has use as an antibiotic, and can be combined with pharmaceutically acceptable carriers and administered internally.

Chelation of silver in accordance with the present invention prevents protein precipitation of silver at or below $10^{-4}$M concentration and obviates silver ED2A and silver ED3A by-products.

EXAMPLE 1

22.4 g of 98% lauroyl chloride were added to 111 g of trisodium salt of ethylenediaminetriacetic acid (27%), with vigorous stirring. Prior to the addition of the lauroyl chloride, 20 g of isopropyl alcohol was added to the ED3ANa$_3$ solution. The reaction mix exothermed to 55° C. upon the addition of the fatty acid chloride. The solution was analyzed by HPLC and 0.04 moles of the fatty acid chloride were found to react to produce 0.04M of free fatty acid, as lauric acid.

EXAMPLE 2

20 g of lauroyl chloride (98%) was added dropwise over 10 minutes to a 115 g ED3ANa$_3$ (27%) solution to which 20 g of isopropyl alcohol was added prior to the lauroyl chloride addition, with vigorous stirring. The temperature was maintained at 20° C. throughout the reaction. Twelve hours later the sample was analyzed for free lauric acid by HPLC, and 0.2M of lauric acid were found, indicating relatively high conversion to lauroyl ED3ANa$_3$.

EXAMPLE 3

20 g of isopropyl alcohol were added to 157.8 g of a 38% ED3ANa$_3$ solution. 17.7 g of nonanoyl chloride were added dropwise over 10 minutes to the ED3ANa$_3$ solution with vigorous stirring. The temperature prior to the addition was 25° C. and on completion of the fatty acid chloride addition was 35° C. The solution was stirred for 35 minutes and acidified to a pH of 4.3 with sulfuric acid. The solution split into two layers.

EXAMPLE 4

20 g of isopropyl alcohol were added to 158 g of a 38% ED3ANa$_3$ solution. 30.1 g of oleoyl chloride were added to the ED3A solution dropwise with vigorous stirring over approximately 10 minutes. During the reaction, the viscosity of the solution began to increase and stirring became difficult. Therefore, 50 g of H$_2$O were added to the reaction to help thin the solution and allow for easier mixing. The solution was allowed to stir overnight, and was then acidified to a pH of 2.5 with H$_2$SO$_4$. An emulsion was formed, which appeared to break upon further dilution with 100 g of H$_2$O, and a light waxy white solid was filtered off.

EXAMPLE 5

20 g of isopropyl alcohol were added to 158 g of a 38% solution of ED3ANa$_3$. 24.7 g of myristoyl chloride were added dropwise over 15 minutes. The solution was stirred for 1 hour. More isopropyl alcohol/H$_2$O (50/50 wt/wt) was added to prevent the solution from gelling, based on visual observation. The solution was acidified to a pH of approximately 2.5 with H$_2$SO$_4$, and a white waxy solid was filtered off.

EXAMPLE 6

18 g of isopropyl alcohol were added to a 144 g of a 25% solution of ED3ANa$_3$. 26.3 g of lauroyl chloride were pumped into the solution of ED3ANa$_3$ uniformly over 20 minutes by means of a metering pump. The temperature of the reaction mixture was maintained at 30° C. throughout the addition. The solution was stirred at 30° C. for another 30 minutes after the lauroyl chloride addition was complete. The solution was then acidified with 18.4 g of 96% H$_2$SO$_4$ and heated to approximately 80° C. The reaction mass was then transferred to a 500 ml. jacketed separatory funnel and held at 80° C. for 30 minutes. The contents separated into two layers. 94.8 grams were recovered from the organic layer and was found to contain 3.84% lauric acid by HPLC. The bottom layer was discarded. Further analysis of the organic layer by HPLC confirmed that lauroyl ED3AH$_3$ was indeed synthesized.

EXAMPLE 7

Example 6 was repeated except that the reaction temperature was maintained at 40° C. During acidification, 22.66 g of 96% H$_2$SO$_4$ were used. The weight of the organic layer recovered was 68.8 g and was found to contain 4.49% lauric acid.

EXAMPLE 8

Example 7 was repeated except that the reaction temperature was maintained at 50° C. The weight of the organic layer recovered was 67.1 g containing 11.34% lauric acid.

In all of the above examples, the product isolated was confirmed to consist primarily of N-acyl ED3AH$_3$ and some free fatty acid, or salts thereof. Solid samples, in the acid form, were recrystallized from isopropyl alcohol and isooctane to remove the free fatty acid. Analysis of the recrystallized materials by NMR confirmed the N-acyl ED3A structures. Analysis by HPLC for free fatty acid on these recrystallized samples were all found to be well below the detection point of approximately 0.1% fatty acid.

EXAMPLE 9

0.8 g of silver acetate hydrate was dissolved in 22 g of a 30% aqueous solution of disodium lauroyl ethylenediaminetriacetic acid using mechanical stirring and sonication (with a Branson 2200 Sonicator Bath). The solution was kept warm at 50° C. as 2 minutes of sonication was alternated with 1 minute of stirring for approximately one hour. The resultant clear amber 2% silver chelating and surfactant solution was transferred to a glass vial and stored in the dark at room temperature (25° C.) for two weeks prior to use.

EXAMPLE 10

1.35 g of silver carbonate, dihydrate, were dissolved in 22 g of a 30% aqueous solution of diammonium lauroyl ED3A using mechanical stirring and heat. The solution was heated to 90° C. and as ammonia degassed with resultant increase of acidity, silver carbonate was dissolved in the solution. After the silver carbonate was completely dissolved, the solution was cooled to stabilize the solution. The resultant solution was transferred to a glass vial and stored in the dark at room temperature (25° C.).

EXAMPLE 11

One g of silver powder was dissolved in 49 g of ED3A acid using mechanical stirring and heat. The solution was kept warm at 80° C. with stirring for approximately 30 days. The resultant solution was transferred to a glass vial and stored in the dark at room temperature.

EXAMPLE 12

Minimum Inhibitory Concentrations (MIC) and Minimum Lethal Concentrations (MLC) of silver LED3A were established by dilution series challenging ATCC (American Type Culture Collection) second generation subcultures of *Escherichia coli, Klebsiella terrigena, Pseudomonas aeruginosa* and *Staphylococcus aureus*. Cultures were maintained and grown according to the methods and media recommended by the ATCC. Serial dilutions of silver LED3A were made in bacterial culture medium from 1× to 800× for *Pseudomonas aeruginosa* and *Staphylococcus aureus* challenges and from 100× to 3200× for *Escherichia coli*. Bacteria were grown in broth and the second generation subculture was diluted with sterile culture medium to between $5\times10^6$ and $5\times10^8$ CFU/ml. Aliquots were taken from the diluted challenge culture in order to maintain consistent CFU/ml across all dilutions of the silver compound. Serial dilutions of 2% silver LED3A (9.9 ml each) were made and 0.1 ml vortexed bacterial suspension was added such that the final test solution contained $5\times10^4$ to $5\times10^6$ CFU/ml with the diluted compound. Population level of each suspension was checked by incubation and cell count. Controls were incubated without silver LED3A addition, but 0.1 ml of medium was added. Samples and cultures were shaken, incubated, compared and subcultured. With growth apparent in the control tube, the status of each challenge to the culture was evaluated for MIC and MLC where growth was rated as: positive, equal to the control; positive, with inhibited growth less than control; or negative, with no growth. The lowest concentration of the silver LED3A which shows marked inhibition of growth in the initial dilution series is deemed the minimum inhibitory concentration (MIC). The lowest concentration of the test material for which no growth occurs on subculture is deemed the minimum lethal concentration (MLC).

The results of the challenge showed:

| Organism | MIC of Silver | MLC of Silver |
|---|---|---|
| *Staphylococcus aureus* | 0.005% | 0.02% |
| *Pseudomonas aeruginosa* | 0.005% | 0.005% |
| *Escherichia coli* | 0.001% | 0.001% |
| *Klebsiella terrigena* | 0.001% | 0.001% |

What is claimed is:

1. Silver chelating agent and surfactant of N-acyl ethylenediaminetriacetic acid or salts thereof, wherein said acyl group is a straight or branched aliphatic or aromatic group containing from 1 to 40 carbon atoms.

2. The silver chelating agent and surfactant of N-acyl ethylenediaminetriacetic acid or salts according to claim 1, wherein said acyl group is a derivative of a carboxylic acid and contains 1 to 40 carbon atoms.

3. The silver chelating agent and surfactant of N-acyl ethylenediaminetriacetic acid or salts according to claim 1, wherein said salts are alkali metal salts.

4. Silver chelating agent and surfactant of lauroyl ethylenediaminetriacetic acid or salts thereof.

5. The silver chelating agent and surfactant of claim 4, wherein said salt is the sodium salt.

6. The silver chelacting agent and surfactant of claim 4, wherein said salt is the ammonium salt.

7. The silver chelating agent and surfactant of claim 4, wherein said salt is the potassium salt.

8. Silver chelating agent and surfactant of ethylenediaminetriacetic acid or salts thereof.

9. The silver chelating agent and surfactant of ethylenediaminetriacetic acid or salts according to claim 8, wherein said salts are alkali metal salts.

10. The silver chelating agent and surfactant of claim 9, wherein said salt is the sodium salt.

11. The silver chelating agent and surfactant of claim 9, wherein said salt is the ammonium salt.

12. The silver chelating agent and surfactant of claim 9, wherein said salt is the potassium salt.

13. Silver chelating agent and surfactant of N-alkyl ethylenediaminetriacetic acid or salts thereof, wherein said alkyl group contains from 1 to 40 carbon atoms.

* * * * *